(12) United States Patent
Briggs et al.

(10) Patent No.: US 7,351,416 B2
(45) Date of Patent: Apr. 1, 2008

(54) **VACCINES COMPRISING ACAPSULAR *P. MULTOCIDA HYAE* DELETION MUTANTS**

(75) Inventors: Robert E. Briggs, Boone, IA (US); Fred M. Tatum, Ames, IA (US)

(73) Assignee: The United States of America as represented by the Department of Agriculture, Washington, DC (US)

( * ) Notice: Subject to any disclaimer, the term of this patent is extended or adjusted under 35 U.S.C. 154(b) by 383 days.

(21) Appl. No.: 10/882,666

(22) Filed: Jul. 2, 2004

(65) Prior Publication Data

US 2005/0106185 A1 May 19, 2005

Related U.S. Application Data

(60) Provisional application No. 60/608,931, filed on Jul. 2, 2003.

(51) Int. Cl.
*A61K 39/102* (2006.01)
(52) U.S. Cl. ............. 424/255.1; 424/235.1; 424/185.1; 435/243; 435/252.3; 435/320.1; 435/172.1
(58) Field of Classification Search ............ 424/255.1, 424/235.1, 185.1; 435/243, 252.3, 320.1, 435/172.1
See application file for complete search history.

(56) References Cited

U.S. PATENT DOCUMENTS

| | | | |
|---|---|---|---|
| 4,169,886 A | 10/1979 | Hertman et al. | |
| 6,326,001 B1 | 12/2001 | Inzana et al. | |
| 2001/0018055 A1 | 8/2001 | Briggs et al. | |
| 2004/0029129 A1* | 2/2004 | Wang et al. ................. | 435/6 |

FOREIGN PATENT DOCUMENTS

| | | | |
|---|---|---|---|
| EP | 1350796 A | 10/2003 | |
| WO | 02/77813 | * 10/2002 | |
| WO | WO 03/086277 A | 10/2003 | |

OTHER PUBLICATIONS

Snipes et al (1987. Avian Diseases 31 (2): p. 254-259 1987. Abstract only at this time.*
Snipes et al (Avian Diseases. 1986. vol. 30 (3): p. 500-504).*
Adler et al., "Candidate vaccine antigens and genes in *Pasteurella multocida*," *J. Biotechnol.* 73, 83-90, 1999.
Boyce et al., "*Pasteurella multocida* capsule: composition, function and genetics," *J. Biotechnol.* 83, 153-60, 2000.
Boyce et al., "Genetic organisation of the capsule biosynthetic locus of *Pasteurella multocida* M1401 (B:2)," *Vet. Microbiol.* 72, 121-34, 2000.
Boyce & Adler, "The Capsule Is a Virulence Determinant in the Pathogenesis of *Pasteurella multocida* M1401 (B:2)," *Inf. Immun.* 68, 3463-68, 2000.
Boyce & Adler, "Acapsular *Pasteurella multocida* B:2 Can Stimulate Protective Immunity against Pasteurellosis," *Inf. Immun.* 69, 1943-46, 2001.
Chung et al., "The capsule biosynthetic locus of *Pateurella multocida* A:1," *FEMS Microbiol. Lett.* 166, 289-96 (1998).
Chung et al., "Role of Capsule in the Pathogenesis of Fowl Cholera Caused by *Pasteurella multocida* Serogroup A," *Inf. Immun.* 69, 2487-92, 2001.
Townsend et al., "Genetic Organization of *Pasteurella multocida cap* Loci and Development of a Multiplex Capsular PCR Typing System," *J. Clin. Microbiol.* 39, 924-29, Mar. 2001.

* cited by examiner

*Primary Examiner*—Jennifer Graser
(74) *Attorney, Agent, or Firm*—Banner & Witcoff, Ltd.

(57) ABSTRACT

Acapsular hyaE deletion mutants of *P. multocida* can be administered to mammals, particularly ungulates, or birds to provide protective immunity against wild-type *P. multocida*, e.g., to prevent or reduce the severity of hemorrhagic septicemia or pneumonia in mammals, particularly livestock, ungulates, and companion animals, or fowl cholera in birds, particularly poultry.

78 Claims, 2 Drawing Sheets

FIG. 1A

SEQUENCE LISTING

<160> NUMBER OF SEQ ID NOS: 9

<210> SEQ ID NO 1
<211> LENGTH: 23
<212> TYPE: DNA
<213> ORGANISM: P. multocida

<400> SEQUENCE: 1
atgaaaaagg ttaatatcat tgg                          23

<210> SEQ ID NO 2
<211> LENGTH: 24
<212> TYPE: DNA
<213> ORGANISM: P. multocida

<400> SEQUENCE: 2
ttaaccttgc ttgaatcgtt tacc                         24

<210> SEQ ID NO 3
<211> LENGTH: 30
<212> TYPE: DNA
<213> ORGANISM: P. multocida

<400> SEQUENCE: 3
aaagatatct tggtttactt caataatttc                   30

<210> SEQ ID NO 4
<211> LENGTH: 33
<212> TYPE: DNA
<213> ORGANISM: P. multocida

<400> SEQUENCE: 4
aaagatatca ctgcatctgt tcaatcaacg agc               33

<210> SEQ ID NO 5
<211> LENGTH: 1870
<212> TYPE: DNA
<213> ORGANISM: P. multocida

<400> SEQUENCE: 5
tatgaaaaag gttattatca ttggacataa acagtctaac tatcaagatg ttgaaaaggt    60
ttttcaatgt tatgggatga atcccccgct tccatcaaaa cgtgaaaaaa tgtcccccat   120
cgaaattggc catgtgctta ataaagtatt accaagtctt gagcacacac ctaaaaatgt   180
atctttactt tctaataaga aaagcaaaat aaaaaaaggg aattcagcca aaaataaatc   240
tcataagcac gctaaaacga acacaataca aacgacttcg agcatctggg ataacttatc   300

-continued

```
tctcgatttg atgctcgcga atatcgagca aaattttggg ggatggtctg atcctaatgc      360
aattcaaata ttagattatt gggctaacct tgacccaaac attcatttcg tctttgttta      420
tgataagcca gaaaatttat tccaatatca tagcttagaa gaggctctca aattagataa      480
acacaccgta caagaaaaat ttgaagagtg gcaaacctac aatgaaaaaa tcctaactta      540
ctttaataaa tataaagatc gtagtgtatt actgaataca caacaactcc aaaatactaa      600
aaaaacatca ctgtctgaaa tttataaaca tatttctgca cctgatgcat tagtcaaaaa      660
actgaatgaa ccttctctaa ataaagagat ggaaattatt gaagtaaacc aagatttatc      720
tcaccaagaa gaatgtccac tgtctaactt tattgttagc caaattataa aaaattctcc      780
tactgttacg caggtatatg aagaattaca gtcgcatgct gatctgcctt atatttcaga      840
acaaaaatta gtaaatgatg ccgattttgc tctccttgca tggaaagata tgattcaaaa      900
acaagtcgat gcaaatcaat atcaacatga aaagaatta gaacttagca caataaaaga      960
acgtcaatta gaggtcacag agaaatatca attgacggaa caaaaactgt cagaaacaca     1020 aaagaaatc gaacaaatta agatgaaaa tagaaaagta aatctgaaa aagcaaaact     1080 cactgcatct gttcaatcaa cgagcaaaat actttctgag aaagaaaaag agatttcttg     1140
cataaaaagt gaaaatacaa agattaaaga agaaaaaatt aaaattgatg aagcatacca     1200
cttaaccaag aaaaccttgt cggataaaga aaaagccctc aaaacgcatc aagatgaaat     1260
tgaagcgctc aagataattt ttaatgaaaa tatttccgta caagaagata tgcaagaaaa     1320
atttcaggaa accaataaaa gaaaacaaga acttgaacaa gagctaaaag ccatatcgga     1380
taagaaagca ttattagaaa cagaaaacag ccaaaaaacc caagtatctg agtctttaga     1440
aaatgaaaat aaagtgttat tagctcaact ccaactcatt caagaagaat tagaaaaact     1500
ttatattgac aatcaagtat taaaagctaa accacgcctt tacggtgcag ctgatcgcat     1560
aaaaaaccaa ttaacttatc gactaggtta caaaatacaa agacatggaa gaagtctatt     1620
tggtctcatt tttcttcctt tcatcttatt tttcacctat ctgggcttta aagagagat     1680 gaaaagtac gaatggaata ccctcccacc aattcacgag tatgaagacg cgcataaagc     1740
aaaccgcatt aaaagccatt tatcttataa attgggtgtc atcttttac aagaaatcaa     1800 aaatccgttt aagtggctta ctctccctta caaactgatt aagaaggta aacgattcaa     1860 gcaaggttaa                                                            1870
```

<210> SEQ ID NO 6
<211> LENGTH: 1870
<212> TYPE: DNA
<213> ORGANISM: P. multocida

<400> SEQUENCE: 6

```
tatgaaaaag gttattatca ttggacataa acagtctaac tatcaagatg ttgaaaaggt     60
ttttcaatgt tatgggatga atcccccgct tccatcaaaa cgtgaaaaaa tgtcccccat    120
cgaaattggc catgtgctta ataaagtatt accaagcctt gagcacacac ctaaaaatgt    180
atctttactt tctaataaga aaagcaaaat aaaaaaaggg aattcagcca aaaataaatc    240
tcataagcac gctaaaacga acacaataca aacgacttcg agcatctggg ataacttatc    300
tctcgatttg atgctcgcga atatcgagcg aaatttttgg ggatggtctg atcctaatgc    360
aattcaaata ttagattatt gggctaacct cgacccaaac attcatttcg tctttgttta    420
tgataagcca gaaaatttat tccaatatca tagcttagaa gaggctctca aattagataa    480
acacaccgta caagaaaaat ttgaagagtg gcaaacctac aatgaaaaaa tcctaactta    540
```

```
ctttaataaa tataaagatc gtagtgtatt actgaataca caacaactcc aaaatactaa        600
aaaaacatca ctgtctgaaa tttataaaca tatttctgca cctgatgcat tagtcaaaaa        660
actgaatgaa ccttctctaa ataaagagat ggaaattatt gaagtaaacc aagatttatc        720
tcaccaagaa gaatgtccac tgtctaactt tattgttagc caaattataa aaaattctcc       780
tactgttacg caggtatatg aagaattaca gtcgcatgct gatctgcctt atatttcaga        840
acaaaaatta gtaaatgatg ccgattttgc tctccttgca tggaaagata tgattcaaaa        900
acaagtcgat gcaaatcaat atcaacatga aaaagaatta gaacttagca caataaaaga        960
acgtcaatta gaggtcacag agaaatatca attgacggaa caaaaactgt cagaaacaca       1020
aaaagaaatc gaacaaatta agatgaaaa tagaaaagta aatctgaaa aagcaaaact         1080 cactgcatct gttcaatcaa cgagcaaaat actttctgag aaagaaaag agatttcttg        1140 cataaaaagt gaaaatacaa agattaaaga agaaaaaatt aaaattgatg aagcatacca      1200
cttaaccaag aaaaccttgt cggataaaga aaaagccctc aaaacgcatc aagatgaaat      1260
tgaagcgctc aagataattt ttaatgaaaa tatttccgta caagaagata tgcaagaaaa     1320
atttcaggaa accaataaaa gaaaacaaga acttgaacaa gagctaaaag ccatatcgga      1380
taagaaagca ttattagaaa cagaaaacag ccaaaaaacc caagtatctg agtctttaga     1440
aaatgaaaat aaagtgttat tagctcaact ccaactcatt caagaagaat tagaaaaact      1500
ttatattgac aatcaagtat taaaagctaa accacgcctt tacggtgcag ctgatcgcat     1560
aaaaaaccaa ttaacttatc gactaggtta caaaatacaa agacatggaa gaagtctatt     1620
tggtctcatt tttcttcccc ttatcttatt ttgcacttat ttgcgtttta aaaagagat      1680 gaaaaagtac gaatggaata ccctcccacc aattcacgag tatgaagacg cgcataaagc      1740
aaaccgcatt aaaagccatt tatcttataa attgggtgtc atcttttac aagaaatcaa       1800 aaatccgttt aagtggctta ctctccctta caaactgatt aaagaaggta acgattcaa      1860 gcaaggttaa                                                            1870

<210> SEQ ID NO 7
<211> LENGTH: 1507
<212> TYPE: DNA
<213> ORGANISM: P. multocida

<400> SEQUENCE: 7
tatgaaaaag gttattatca ttggacataa acagtctaac tatcaagatg ttgaaaaggt         60
ttttcaatgt tatgggatga atcccccgct tccatcaaaa cgtgaaaaaa tgtcccccat        120
cgaaattggc catgtgctta ataaagtatt accaagtctt gagcacacac ctaaaaatgt       180
atctttactt tctaataaga aaagcaaaat aaaaaaaggg aattcagcca aaaatctaaatc     240 tcataagcac gctaaaacga acacaataca aacgacttcg agcatctggg ataacttatc      300
tctcgatttg atgctcgcga atatcgagca aaatttttgg ggatggtctg atcctaatgc      360
aattcaaata ttagattatt gggctaacct tgacccaaac attcatttcg tctttgttta     420
tgataagcca gaaaatttat tccaatatca tagcttagaa gaggctctca aattagataa    480
acacaccgta caagaaaaat ttgaagagtg gcaaacctac aatgaaaaaa tcctaactta    540
ctttaataaa tataaagatc gtagtgtatt actgaataca caacaactcc aaaatactaa     600
aaaaacatca ctgtctgaaa tttataaaca tatttctgca cctgatgcat tagtcaaaaa    660
actgaatgaa ccttctctaa ataaagagat ggaaattatt gaagtaaacc aagatatcac    720
tgcatctgtt caatcaacga gcaaaatact ttctgagaaa gaaaaagaga tttcttgcat   780
```

-continued

```
aaaaagtgaa atacaaaga ttaaagaaga aaaaattaaa attgatgaag cataccactt      840
aaccaagaaa accttgtcgg ataaagaaaa agccctcaaa acgcatcaag atgaaattga      900
agcgctcaag ataatttta atgaaaatat ttccgtacaa gaagatatgc aagaaaaatt      960
tcaggaaacc aataaaagaa acaagaact tgaacaagag ctaaaagcca tatcggataa     1020
gaaagcatta ttagaaacag aaaacagcca aaaaacccaa gtatctgagt ctttagaaaa     1080
tgaaaataaa gtgttattag ctcaactcca actcattcaa gaagaattag aaaaacttta     1140
tattgacaat caagtattaa aagctaaacc acgcctttac ggtgcagctg atcgcataaa     1200
aaaccaatta acttatcgac taggttacaa aatacaaaga catggaagaa gtctatttgg     1260
tctcattttt cttcctttca tcttattttt cacctatctg ggctttaaaa gagagatgaa     1320
aaagtacgaa tggaatacccc tcccaccaat tcacgagtat gaagacgcgc ataaagcaaa     1380
ccgcattaaa agccatttat cttataaatt gggtgtcatc ttttacaag aaatcaaaaa     1440 tccgtttaag tggcttactc tcccttacaa actgattaaa gaaggtaaac gattcaagca     1500
aggttaa                                                              1507
```

<210> SEQ ID NO 8
<211> LENGTH: 1531
<212> TYPE: DNA
<213> ORGANISM: P. multocida

<400> SEQUENCE: 8

```
tatgaaaaag gttattatca ttggacataa acagtctaac tatcaagatg ttgaaaaggt       60
ttttcaatgt tatgggatga atcccccgct tccatcaaaa cgtgaaaaaa tgtcccccat      120
cgaaattggc catgtgctta ataaagtatt accaagcctt gagcacacac ctaaaaatgt      180
atctttactt tctaataaga aaagcaaaat aaaaaaaggg aattcagcca aaaataaatc      240
tcataagcac gctaaaacga acacaataca acgacttcg agcatctggg ataacttatc      300
tctcgatttg atgctcgcga atatcgagcg aaattttggg ggatggtctg atcctaatgc      360
aattcaaata ttagattatt gggctaacct cgacccaaac attcattcg tctttgttta      420 tgataagcca gaaaatttat tccaatatca tagcttagaa gaggctctca aattagataa      480
acacaccgta caagaaaaat tgaagagtg gcaaacctac aatgaaaaaa tcctaactta      540
ctttaataaa tataaagatc gtagtgtatt actgaataca caacaactcc aaaatactaa      600
aaaaacatca ctgtctgaaa tttataaaca tatttctgca cctgatgcat tagtcaaaaa      660
actgaatgaa ccttctctaa ataaagagat ggaaattatt gaagtaaacc aagatccccg      720
gggccccggg gccccgggga tcactgcatc tgttcaatca acgagcaaaa tactttctga      780
gaaagaaaaa gagatttctt gcataaaaag tgaaaataca aagattaaag aagaaaaaat      840
taaaattgat gaagcatacc acttaaccaa gaaaaccttg tcggataaag aaaaagccct      900
caaaacgcat caagatgaaa ttgaagcgct caagataatt tttaatgaaa atatttccgt      960
acaagaagat atgcaagaaa aatttcagga aaccaataaa agaaacaag aacttgaaca     1020 agagctaaaa gccatatcgg ataagaaagc attattagaa acagaaaaca gccaaaaaac     1080
ccaagtatct gagtctttag aaaatgaaaa taaagtgtta ttagctcaac tccaactcat     1140
tcaagaagaa ttagaaaaac tttatattga caatcaagta ttaaaagcta aaccacgcct     1200
ttacggtgca gctgatcgca taaaaaacca attaacttat cgactaggtt acaaaataca     1260
aagacatgga agaagtctat ttggtctcat ttttcttccc cttatcttat tttgcactta     1320
tttgcgtttt aaaaaagaga tgaaaaagta cgaatggaat accctcccac caattcacga     1380
```

-continued

```
gtatgaagac gcgcataaag caaaccgcat taaaagccat ttatcttata aattgggtgt    1440
catcttttta caagaaatca aaaatccgtt taagtggctt actctccctt acaaactgat    1500
taaagaaggt aaacgattca agcaaggtta a                                   1531
```

<210> SEQ ID NO 9
<211> LENGTH: 8
<212> TYPE: PRT
<213> ORGANISM: Artificial Sequence
<220> FEATURE:
<223> OTHER INFORMATION: synthesized sequence

<400> SEQUENCE: 9

Pro Arg Gly Pro Gly Ala Pro Gly
 1               5

VACCINES COMPRISING ACAPSULAR P. MULTOCIDA HYAE DELETION MUTANTS

This application claims the benefit of and incorporates by reference to now abandoned provisional application Ser. No. 60/608,931 filed Jul. 2, 2003.

FIELD OF THE INVENTION

The invention relates to acapsular mutants of *Pasteurella multocida* and vaccines comprising the mutants.

BACKGROUND OF THE INVENTION

*Pasteurella multocida* (*P. multocida*) is associated with a variety of diseases, including calf and yearling meningoencephalitis, lamb lymphadenitis, horse and donkey septicemia, bovine septicemic pasteurellosis (hemorrhagic septicemia, barbone), swine pasteurellosis, porcine septicemic pasteurellosis, pneumonia, and fowl cholera.

There is a need in the art for effective vaccines that can be used to provide protective immunity against diseases caused by *P. multocida*.

SUMMARY OF THE INVENTION

One embodiment of the invention is an isolated *Pasteurella multocida* (*P. multocida*) bacterium of serogroup A which comprises a deletion of all or a part of a hyaE gene. The deletion attenuates the bacterium.

Another embodiment of the invention is a vaccine for inducing protective immunity against wild-type *P. multocida*. The vaccine comprises *P. multocida* bacterium of serogroup A which comprises a deletion of all or a part of a hyaE gene and a pharmaceutically acceptable vehicle. The deletion mutation attenuates the bacterium.

Yet another embodiment of the invention are feeds suitable for mammals (including livestock, ungulates, and companion animals or birds (preferably poultry) comprising a *P. multocida* bacterium of serogroup A which comprises a deletion of all or a part of a hyaE gene. The mutation attenuates the bacterium.

Even another embodiment of the invention is a method of inducing protective immunity against wild-type *P. multocida*. A *P. multocida* bacterium of serogroup A is administered to an animal subject such as a mammal (including livestock, ungulates, and companion animals) or a bird (including poultry). The bacterium comprises a deletion of all or a part of a hyaE gene, which attenuates the bacterium. The bacterium thereby confers to the animal subject protective immunity against wild-type *P. multocida*.

The invention thus provides tools and methods for inducing protective immunity against diseases caused by *P. multocida*.

BRIEF DESCRIPTION OF THE FIGURE

FIG. 1. Illustration of the construction of hyaE deletion mutants.

DETAILED DESCRIPTION OF THE INVENTION

Figure 1A:
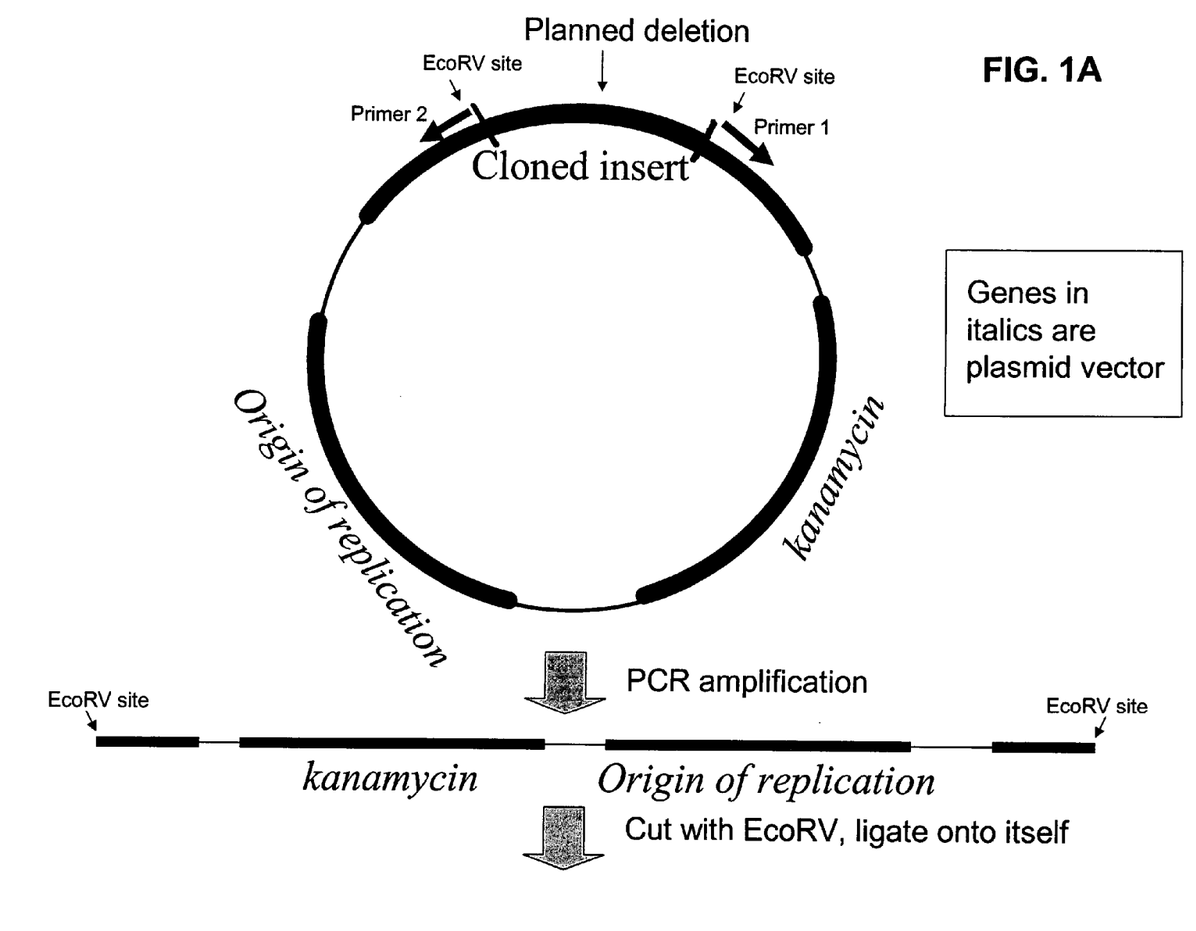
FIG. 1A, schematic showing planned deletion.
Figure 1B:
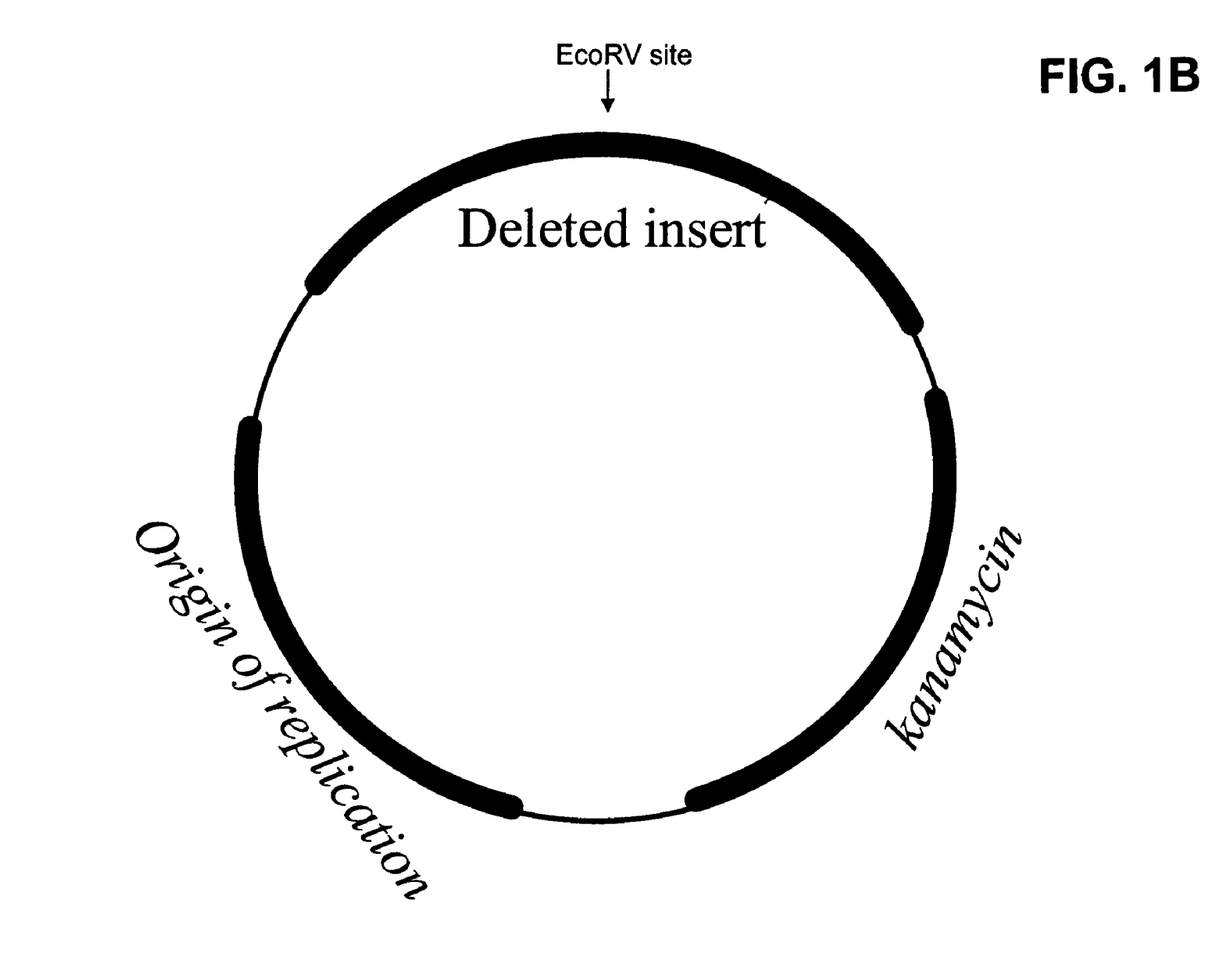
FIG. 1B, plasmid containing deleted hyaE insert.

Acapsular hyaE deletion mutants of *P. multocida* serogroup A can be administered to mammals (including livestock, ungulates, and companion animals) and birds (including poultry) to provide protective immunity against wild-type *P. multocida*, e.g., to prevent or reduce the severity of diseases such as hemorrhagic septicemia or pneumonia in livestock, ungulates, and companion animals and to prevent or reduce the severity of fowl cholera in birds, especially poultry, respectively. The terms "acapsular mutant(s)," "acapsular bacterium(a)," and "mutant bacterium(a)" are used interchangeably in this description.

Acapsular hyaE Deletion Mutants of *P. Multocida* Serogroup A

Acapsular hyaE deletion mutants of serogroup A *P. multocida* (e.g., serotypes A:1, A:3, A:4) can be generated by mutagenizing the hyaE gene in the capsule biosynthetic locus. The genes of the capsule biosynthetic locus in serogroup A are well known and have been completely sequenced. Chung et al., *FEMS Microbiol. Lett.* 166(2), 289-96, 1998. The serotype A:1 locus contains four open-reading frames (ORFs) in region 1 (hexA, hexB, hexC, and hexD), five ORFs in region 2 (hyaA, hyaB, hyaC, hyaD, and hyaE), and two ORFs in region 3 (phyA and phyB).

In certain embodiments, the mutant bacteria do not comprise any antibiotic resistance genes or foreign DNA, which improves their environmental and ecological attractiveness. A method of generating deletion mutants is described in Example 1, but any other methods known in the art can be used to generate deletion mutations. Simple tests for confirming that mutants have an acapsular phenotype also are disclosed in Example 1.

*P. multocida* bacteria with any deletion of all or a part of the hyaE gene is within the scope of the invention so long as the deletion attenuates the bacterium. In one embodiment, the deletion mutation results in the deletion of amino acids 239-359 of the hyaE protein (i.e., none of amino acids 239-359 are present in the encoded hyaE protein). In other embodiments, the mutated hyaE open reading frame comprises SEQ ID NO:7 or SEQ ID NO:8.

A mutant bacterium is attenuated if, after exposure to the mutant bacterium, an increase in the dosage of wild-type *P. multocida* is required to kill half the susceptible target species (i.e., the $LD_{50}$ increases) and/or there is a reduction in pathologic lesions (e.g., pneumonia) after exposure of the target species to the mutant bacterium compared with exposure to a wild-type bacterium, and/or there is a reduction in commensal colonization of mucosal surfaces where *P. multocida* reside after exposure of the target species to the mutant bacterium when compared with exposure to a wild-type bacterium.

Attenuation can be assessed by various means as is known in the art. For example, for septiceaemic disease (such as fowl cholera), susceptible species can be exposed to wild-type organisms by intranasal, intravenous, intramuscular, or intraperitoneal routes, and the dosage required to cause disease between wild-type and mutant organisms can be compared. For pneumonic disease, one can expose susceptible animals to wild-type organisms by intranasal, intratracheal, or intrapulmonic routes and compare the extent and severity of clinical symptoms and pathologic lesions between mutant- and wild-type-exposed animals. For mucosal colonization, animals can be exposed to wild-type organisms by oral, intranasal, or intratonsillar routes and the numbers of organisms recovered from nasal mucus or tonsillar wash specimens at intervals after exposure can be compared.

Vaccine Preparations

Vaccines comprising mutant bacteria can be given alone or as a component of a polyvalent vaccine, i.e., in combination with other vaccines. Mutant bacteria in a vaccine formulation can be live or killed; either live or killed bacteria can be lyophilized and, optionally, reconstituted as is known in the art. Vaccines can conveniently be provided in kits, which also can comprise appropriate labeling and instructions for administering a vaccine to an animal subject (e.g., livestock, an ungulate, a companion animal) or a bird (e.g., poultry).

Vaccines comprising acapsular mutants also can comprise pharmaceutically and veterinarily acceptable carriers. Such carriers are well known to those in the art and include, but are not limited to, large, slowly metabolized macromolecules, such as proteins, polysaccharides, polylactic acids, polyglycolic acids, polymeric amino acids, amino acid copolymers, and inactive virus particles. Pharmaceutically and veterinarily acceptable salts can also be used in the vaccine, for example, mineral salts such as hydrochlorides, hydrobromides, phosphates, or sulfates, as well as the salts of organic acids such as acetates, proprionates, malonates, or benzoates. Vaccines also can contain liquids, such as water, saline, glycerol, and ethanol, as well as substances such as wetting agents, emulsifying agents, or pH buffering agents. Liposomes also can be used as carriers for mutant bacteria. See U.S. Pat. No. 5,422,120, WO 95/13796, WO 91/14445, or EP 524,968 B1.

If desired, an adjuvant can be added to a vaccine. Useful adjuvants include, without limitation, surfactants (e.g., hexadecylamine, octadecylanine, lysolecithin, dimethyldioctadecylammonium bromide, N,N-dioctadecyl-n'-N-bis(2-hydroxyethylpropane di-amine), methoxyhexadecylglycerol, and pluronic polyols); polyanions (e.g., pyran, dextran sulfate, poly IC, polyacrylicacid, carbopol), peptides (e.g., muramyl dipeptide, dimethylglycine, tuftsin), oil emulsions, alum, and mixtures thereof.

Treatment of Mammals, Particularly Livestock, Ungulates, and Companion Animals

"Mammals" include monotremes (e.g., platypus), marsupials (e.g., kangaroo), and placentals, which include livestock (domestic animals raised for food, milk, or fiber such as hogs, sheep, cattle, and horses) and companion animals (e.g., dogs, cats). "Ungulates" include, but are not limited to, cattle (bovine animals), water buffalo, bison, sheep, swine, deer, elephants, and yaks. Each of these includes both adult and developing forms (e.g., calves, piglets, lambs, etc.). Bacteria of the invention can be administered either to adults or developing mammals, preferably livestock, ungulates, or companion animals.

A convenient method of delivering a bacterium of the invention to mammals (such as livestock, ungulates, or companion animals) is by oral administration (e.g., in the feed or drinking water or in bait). It is particularly convenient to top-dress or mix feed with the bacteria. Typically, large animals (e.g., livestock/ungulates such as cattle) are dosed with about $10^6$, $5\times10^6$, $10^7$, $5\times10^7$, $10^8$, $5\times10^8$, $10^9$, $5\times10^9$, or $10^{10}$ cfu; about $10^8$, $5\times10^8$, $10^9$, $5\times10^9$ cfu if feed is top-dressed. Doses of about $10^6$ to about $10^8$, about $2\times10^6$ to about $3\times10^8$, about $2.4\times10^6$ to about $2.6\times10^8$, about $10^4$ to about $10^6$ cfu or of about $10^4$ to about $10^9$ cfu can be given. Doses can be adjusted for smaller livestock/ungulates such as sheep (e.g., about $10^4$, $5\times10^4$, $10^5$, $5\times10^5$, $10^6$, $5\times10^6$, $10^7$, $5\times10^7$, $10^8$, $5\times10^8$ cfu). Analogous dosing regimens can be readily deduced for companion animals.

Although the oral route is preferred for ease of delivery, other routes for vaccination can also be used. These include without limitation, subcutaneous, intramuscular, intravenous, intradermal, intranasal, intrabronchial, etc. Bacteria of the invention can be implanted in the ear. Bacteria also can be administered by airspray, by eye inoculation, or by scarification.

Treatment of Birds

"Birds" include wild (e.g., game fowl) and domesticated (e.g., poultry or pet) birds and includes both adult and developing forms (e.g., hatchlings, chicks, poults, etc.). "Poultry" or "poultry birds" include all birds kept, harvested, or domesticated for meat or eggs, including chicken, turkey, ostrich, game hen, squab, guinea fowl, pheasant, quail, duck, goose, and emu.

Bacteria of the invention can be administered to a bird by any known or standard technique, including mucosal or intramuscular injection. In a hatchery, bacteria can be administered using techniques such as in ovo vaccination, spray vaccination, or subcutaneous vaccination. On the farm, bacteria can be administered using techniques such as scarification, spray vaccination, eye drop vaccination, in-water vaccination, in-feed vaccination, wing web vaccination, subcutaneous vaccination, and intramuscular vaccination.

Effective doses depend on the size of the bird. Doses range and can vary, for example, from about $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $10^9$, to $5\times10^9$ cfu.

All patents and patent applications cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Generation of Acapsular hyaE Deletion *P. Multocida* Mutants

*P. multocida* mutants of strains 1059 (avian, serotype A:3) and 1062 (bovine, serotype A:3) were generated by deleting the coding region of their hyaE genes, which blocked synthesis of the capsular building block N-acetyl-D-glucosamine. The coding regions of the 1059 and 1062 hyaE genes (SEQ ID NOS:5 and 6, respectively) were obtained by PCR amplification, using the forward primer 5'-ATGAAAAAGGTTAATATCATTGG-3' (SEQ ID NO:1) and the reverse primer 5'-TTAACCTTGCTTGAATCGTT-TACC-3' (SEQ ID NO:2). All primers were synthesized with an oligonucleotide synthesizer (Applied Biosystems Inc.) by Integrated DNA Technologies, Inc., Coralville, Iowa. The PCR reactions were carried out using the GeneAmp LX PCR Kit (PE Applied Biosystems, Foster City, Calif.) in a Perkin Elmer GeneAmp 9600 thermocycler. Reaction conditions were 30 cycles, with 30 seconds at 95° C., 45 seconds at 48° C., and 60 seconds at 72° C. per cycle.

The two PCR-generated hyaE fragments initiated at their start Met codons and ended at their stop codons. The PCR fragments were ligated into pCR2.1 (Invitrogen Inc., LaJolla, Calif.) and electroporated into the *E. coli* strain DH11S (Life Technologies, Rockville, Md.), which generated the plasmids pCR2.1hyaE1059 and pCR2.1hyaE1062. The two plasmid constructs were isolated by the alkaline SDS method, then purified by CsCl centrifugation using standard methods. Both strands of both hyaE genes were sequenced using the Dye Terminator Chemistry kit from PE Applied Biosystems. Samples were run on an ABI Prism 377 DNA Sequencer by the Nucleic Acids Facility, Iowa State University, Ames, Iowa.

The structural hyaE genes of each strain were 1869 bp in length. Due to sequence variation, primarily found in the 3' end of the coding region, unique hyaE replacement plasmids were constructed for each strain in order to engineer the two mutant strains of *P. multocida*. Precise deletions within each hyaE gene contained on plasmids pCR2.1hyaE1059 and pCR2.1hyaE1062 were achieved by PCR using the deletion primers 5'-AAAGATATCTTGGTTTACTTCAATAATTTC-3' (SEQ ID NO:3) and 5'-AAAGATATCACTGCATCTGT-TCAATCAACGAGC-3' (SEQ ID NO:4). The deletion primers anneal to the cloned gene approximately 300 base-pairs apart but extend outwards, towards the plasmid vector, rather than inwards. The PCR reaction amplifies the entire cloning vector and two ends of the gene insert but not the approximately 300 base pair "deletion." The amplified product is linear, with the two hyaE gene fragments on the ends and plasmid vector in the middle. The primers contain EcoRV sites (GATATC) on their 5' termini. The ends of the linear amplified product, therefore, contain EcoRV sites. See FIGS. 1A and 1B.

The resulting PCR fragments were subjected to EcoRV restriction digestion to remove specific sequences from their ends. Each fragment was then ligated to generate inframe deletions excising nucleotides 715 through 1082. An eight basepair SmaI linker (5'-CCCCGGGG-3') was inserted into the EcoRV deletion site of *P. multocida* 1062 to ensure that the mutation would result in an acapsular phenotype. No such DNA was inserted into the deletion site of the *P. multocida* 1059 hyaE insert.

The nucleotide sequences of the 1059 and 1062 mutated hyaE fragments are shown in SEQ ID NOS:7 and 8, respectively. In both 1059 and 1062, amino acid 239 through amino acid 359 of the hyaE protein were deleted. In addition, in both strains the amino acid at former position 360 was changed from leucine to isoleucine. Strain 1062 received an additional 8 amino acids in the deletion site just upstream from the former position 360 (Pro Arg Gly Pro Gly Ala Pro Gly; SEQ ID NO:9).

The mutated hyaE fragments were subcloned into EcoRI sites within the multiple cloning site of plasmid pBCSK (Strategene Inc.), followed by insertion of the Tn903 kanamycin resistance element into the adjacent BamHI sites to produce pBCSKΔhyaEkan$^r$1059 and pBCSKΔhyaEkan$^r$1062, respectively. Construction of the replacement plasmids were completed by ligating BssH2 generated ΔhyaEkan$^r$ fragments of 1059 and 1062 with the 1.2 kb temperature-sensitive origin of replication of pBB 192 excised from the BssH2 site of pBCSK (Stratagene, Inc.). See U.S. Pat. No. 5,840,556. Because ColE1 origin is inactive in *P. multocida,* only the ligation products generating plasmids p192oriΔhyaEkan$^r$1059 or p192oriΔhyaEkan$^r$1062 were capable of replicating within the hosts.

Replacement plasmids were introduced into the appropriate *P. multocida* strains by electroporation. Cells were grown in Columbia broth, then prepared for electroporation by the following steps. The growth was pelleted by centrifugation at 5000×g for 15 minutes and washed once in 100 ml 272 mM sucrose at 0° C. The cell pellet was resuspended (1:3 packed bacteria: 272 mM sucrose) on ice. Competent bacteria (100 μl) were mixed in a 0.1 cm electroporation cuvette (Bio-Rad) with 200 ng plasmid DNA which was either unmethylated or methylated in vitro using HhaI. Immediately after adding DNA, the cells were electroporated (Gene pulser, Bio-Rad) at 18,000 V/cm, 800 ohm, and 25 mFd, with resultant time constants ranging from 11 to 15 msec.

Columbia broth (1 ml, 0° C.) was added to the electroporated cells, and the resuspensions were incubated at 25° C. for approximately 25 minutes. The cells recovered at 30° C. for 2 hours and were then plated onto Columbia agar plates containing 50 μg/ml kanamycin. Colonies were visible after 24-hour incubation at 30° C. Transformed cells were grown at 30° C. overnight in broth containing kanamycin. The cells were then plated onto dextrose starch agar plates with 50 μg/ml kanamycin and grown at 3° C. for 24 hours.

Cells possessing integrated plasmid survived antibiotic selection at the non-permissive temperature for plasmid replication, and these could be identified because integration of replacement plasmid resulted in an acapsular phenotype. Distinguishing between capsular and acapsular *P. multocida* colonies of strains 1059 and 1062 grown on dextrose starch agar plates was easily accomplished. Wild-type capsular colonies of the two strains possess hyaluronic acid, the major capsule component, which renders colonies mucoid in appearance; when viewed under obliquely transmitted light, these colonies exhibit pearl-like iridescence. In contrast, the acapsular single-crossover mutants are non-mucoid and non-iridescent.

Single-crossover mutants were transferred to 5 ml Columbia broth without antibiotic supplementation and incubated at 30° C. overnight to resolve plasmid from the chromosome. Growth was transferred to dextrose-starch agar plates without supplemental antibiotic which were incubated at 38° C. for 12 hours. The initial test to identify double crossover mutants involved replica-plating arrays of cells that appeared acapsular onto dextrose starch agar plates, either with or without antibiotic, and growing the cells at 38° C. Acapsular colonies that failed to grow on the antibiotic plates were subjected to PCR analysis using the hyaE forward and reverse primers. The sizes of the PCR products were compared to those of the wild-type parent using agarose gel electrophoresis.

Suspected *P. multocida* 1059 and 1062 hyaE deletion mutants were also assayed for the presence of the kanamycin resistance gene. Putative mutants possessing "clean" hyaE deletions were devoid of antibiotic resistance sequences. A disc diffusion enzyme assay (Kirby-Bauer test, Bauer et al., *Am. J. Clin. Path.* 45, 493-96, 1966) and an Indian ink staining assay (Collins & Lyne, MICROBIOLOGICAL METHODS, Butterworths, Boston, Mass., 1976, p. 110) were used to confirm that the two hyaE mutants possessed an acapsular phenotype.

EXAMPLE 2

Vaccination of Turkey Poults with the 1059 ΔhyaE *P. Multocida* Strain

Attenuation of the 1059 ΔhyaE *P. multocida* strain was assessed in three week-old broad-breasted white turkey poults. Groups consisting of four poults were injected intramuscularly with ten-fold serial dilutions of exponential growth-phase cultures of wild-type or acapsular mutant cultures suspended in trypticase broth (0.1 ml). The poults were observed for 7 days after challenge.

The $LD_{50}$ values (i.e., the amount of bacteria needed to kill half the poults) were <$10^3$ organisms for poults injected with the wild-type strain and in excess of $10^7$ organisms for poults injected with the hyaE mutant.

EXAMPLE 3

Vaccination of Steer Calves with the 1062 ΔhyaE *P. Multocida* Strain

Six Holstein steer calves, approximately 500 pounds, were exposed to the 1062 ΔhyaE *P. multocida* acapsular mutant. The strain was administered either by subcutaneous injection in the neck ($10^8$ cfu) or by top-dressing feed ($10^9$ cfu).

No adverse reaction to either exposure was observed. Mucosal vaccinates became colonized in the palatine tonsils for the remainder of the trial (5 weeks). Intratracheal challenge with the virulent parent strain ($10^{10}$ cfu total dose in 15 ml) elicited transient (1-2) day fevers in control calves but little or no pneumonic changes 10 days post-challenge in controls or vaccinates.

EXAMPLE 4

Efficacy Study in 2-3 Month-Old Calves Challenged Transtracheally with Virulent *P. Multocida*

Three groups of male bovine calves (n=15) were vaccinated subcutaneously with a single 2 mL dose of either a $2.6 \times 10^8$ cfu/dose of the 1062 ΔhyaE *P. multocida* acapsular mutant, a $2.4 \times 10^6$ cfu/dose of the mutant, or sterile PBS. At the time of vaccine administration, the average weight of the calves was 70 kg (154 lbs). After 21 days, calves were challenged transtracheally with a live culture of *P. multocida* and observed for 7 days.

The mean lung lesion score for the high dose of *P. multocida* 1062 ΔhyaE was 3.1±2.8%. The mean lung lesion score for the low dose of *P. multocida* 1062 ΔhyaE was 3.7±2.2%, and the mean lung lesion score for the control group was 7.7±5.2%. The median lung lesion score for each vaccine group was significantly lower than the control group; P<0.0006.

The invention claimed is:

1. An isolated *Pasteurellaceae multocida* (*P. multocida*) bacterium of serogroup A which comprises a hyaE gene comprising a deletion in its coding region, wherein the deletion results in an acapsular phenotype of the bacterium, thereby attenuating the bacterium.

2. The bacterium of claim 1 which comprises no antibiotic resistance genes.

3. The bacterium of claim 1 which comprises no exogenous DNA.

4. The bacterium of claim 1 which is serotype A:3.

5. The bacterium of claim 1 which is serotype A:1.

6. The bacterium of claim 1 which is serotype A:4.

7. The bacterium of claim 1 wherein the hyaE gene encodes a hyaE protein in which amino acids 239-359 are deleted, wherein the amino acids are numbered according to the hyaE protein encoded by the nucleotide sequence shown in SEQ ID NO:5.

8. The bacterium of claim 1 wherein the hyaE gene comprising the deletion in its coding region comprises the nucleotide sequence shown in SEQ ID NO:7.

9. The bacterium of claim 1 wherein the hyaE gene comprising the deletion in its coding region comprises the nucleotide sequence shown in SEQ ID NO:8.

10. The bacterium of claim 1 which is live.

11. The bacterium of claim 1 which is lyophilized.

12. The bacterium of claim 1 which is killed.

13. A vaccine for inducing protective immunity against wild-type *P. multocida* comprising:
the bacterium of claim 1; and
a pharmaceutically acceptable vehicle.

14. The vaccine of claim 13 wherein the bacterium comprises no antibiotic resistance genes.

15. The vaccine of claim 13 wherein the bacterium comprises no exogenous DNA.

16. The vaccine of claim 13 wherein the bacterium is serotype A:3.

17. The vaccine of claim 13 wherein the bacterium is serotype A:1.

18. The vaccine of claim 13 wherein the bacterium is serotype A:4.

19. The vaccine of claim 13 wherein the hyaE gene comprising the deletion in its coding region comprises the nucleotide sequence shown in SEQ ID NO:7.

20. The vaccine of claim 13 wherein the hyaE gene comprising the deletion in its coding region comprises the nucleotide sequence shown in SEQ ID NO:8.

21. The vaccine of claim 13 wherein the bacterium is live.

22. The vaccine of claim 13 wherein the bacterium is lyophilized.

23. The vaccine of claim 13 wherein the bacterium is killed.

24. The vaccine of claim 13 which is packaged with instructions for administering the vaccine to an ungulate to confer protective immunity against wild-type *P. multocida*.

25. The vaccine of claim 13 which is packaged with instructions for administering the vaccine to a bird to confer protective immunity against wild-type *P. multocida*.

26. A feed suitable for ungulates comprising the bacterium of claim 1.

27. The feed of claim 26 wherein the bacterium comprises no antibiotic resistance genes.

28. The feed of claim 26 wherein the bacterium comprises no exogenous DNA.

29. The feed of claim 26 wherein the bacterium is serotype A:3.

30. The feed of claim 26 wherein the bacterium is serotype A:1.

31. The feed of claim 26 wherein the bacterium is serotype A:4.

32. The feed of claim 26 wherein the hyaE gene comprising the deletion in its coding region comprises the nucleotide sequence shown in SEQ ID NO:7.

33. The feed of claim 26 wherein the wherein the hyaE gene comprising the deletion in its coding region comprises the nucleotide sequence shown in SEQ ID NO:8.

34. The feed of claim 26 wherein the bacterium is live.

35. The feed of claim 26 wherein the bacterium is lyophilized.

36. The feed of claim 26 wherein the bacterium is killed.

37. The feed of claim 26 which is packaged with instructions for administering the feed to ungulates to confer protective immunity against wild-type *P. multocida*.

38. A feed suitable for a bird comprising the bacterium of claim 1.

39. The feed of claim 38 wherein the bacterium comprises no antibiotic resistance genes.

40. The feed of claim 38 wherein the bacterium comprises no exogenous DNA.

41. The feed of claim 38 wherein the bacterium is serotype A:3.

42. The feed of claim 38 wherein the bacterium is serotype A:1.

43. The feed of claim 38 wherein the bacterium is serotype A:4.

44. The feed of claim 38 wherein the hyaE gene comprising the deletion in its coding region comprises the nucleotide sequence shown in SEQ ID NO:7.

45. The feed of claim 38 wherein the hyaE gene comprising the deletion in its coding region comprises the nucleotide sequence shown in SEQ ID NO:8.

46. The feed of claim 38 wherein the bacterium is live.

47. The feed of claim 38 wherein the bacterium is lyophilized.

48. The feed of claim 38 wherein the bacterium is killed.

49. The feed of claim 38 which is packaged with instructions for administering the feed to a bird to confer protective immunity against wild-type *P. multocida*.

50. A method of inducing protective immunity against wild-type *P. multocida* comprising the step of:
administering the bacterium of claim 1 to an ungulate or a bird, whereby the bacterium confers to the ungulate or bird protective immunity against wild-type *P. multocida*.

51. The method of claim 50 wherein the bacterium comprises no antibiotic resistance genes.

52. The method of claim 50 wherein the bacterium comprises no exogenous DNA.

53. The method of claim 50 wherein the bacterium is serotype A:3.

54. The method of claim 50 wherein the bacterium is serotype A:1.

55. The method of claim 50 wherein the bacterium is serotype A:4.

56. The method of claim 50 wherein the hyaE gene comprising the deletion in its coding region comprises the nucleotide sequence shown in SEQ ID NO shown in SEQ ID NO:7.

57. The method of claim 50 wherein the hyaE gene comprising the deletion in its coding region comprises the nucleotide sequence shown in SEQ ID NO shown in SEQ ID NO:8.

58. The method of claim 50 wherein the bacterium is live.

59. The method of claim 50 wherein the bacterium is lyophilized.

60. The method of claim 50 wherein the bacterium is killed.

61. The method of claim 50 wherein the bacterium is administered to an ungulate.

62. The method of claim 61 wherein the ungulate is a bovine animal.

63. The method of claim 50 wherein the bacterium is administered to a bird.

64. The method of claim 50 wherein the bacterium is administered to a bird and the bird is a poultry bird.

65. The method of claim 50 wherein the bacterium is administered to a bird and the bird is a poultry bird is selected from the group consisting of chicken, turkey, ostrich, game hen, squab, guinea fowl, pheasant, quail, duck, goose, and emu.

66. The method of claim 50 wherein the bacterium is administered to a bird and the bird is a chicken.

67. The method of claim 50 wherein the bacterium is administered to a bird and the bird is a turkey.

68. The method of claim 50 wherein the bacterium is administered subcutaneously.

69. The method of claim 50 wherein the bacterium is administered intramuscularly.

70. The method of claim 50 wherein the bacterium is administered orally.

71. The method of claim 50 wherein the bacterium is administered by top-dressing feed.

72. The method of claim 50 wherein the bacterium is administered intranasally.

73. The method of claim 50 wherein the bacterium is administered at a dose between about $10^4$ and about $10^9$ cfu.

74. The method of claim 50 wherein the dose is between about $10^4$ and about $10^6$ cfu.

75. The vaccine of claim 13, wherein the hyaE gene encodes a hyaE protein in which amino acids 239-359 are deleted, wherein the amino acids are numbered according to the hyaE protein encoded by the nucleotide sequence shown in SEQ ID NO:5.

76. The feed of claim 26 wherein the hyaE gene encodes a hyaE protein in which amino acids 239-359 are deleted, wherein the amino acids are numbered according to the hyaE protein encoded by the nucleotide sequence shown in SEQ ID NO:5.

77. The feed of claim 38 wherein the hyaE gene encodes a hyaE protein in which amino acids 239-359 are deleted, wherein the amino acids are numbered according to the hyaE protein encoded by the nucleotide sequence shown in SEQ ID NO:5.

78. The method of claim 50 wherein the hyaE gene encodes a hyaE protein in which amino acids 239-359 are deleted, wherein the amino acids are numbered according to the hyaE protein encoded by the nucleotide sequence shown in SEQ ID NO:5.

* * * * *

UNITED STATES PATENT AND TRADEMARK OFFICE
CERTIFICATE OF CORRECTION

| | | |
|---|---|---|
| PATENT NO. | : 7,351,416 B2 | Page 1 of 1 |
| APPLICATION NO. | : 10/882666 | |
| DATED | : April 1, 2008 | |
| INVENTOR(S) | : Briggs and Tatum | |

It is certified that error appears in the above-identified patent and that said Letters Patent is hereby corrected as shown below:

In Column 15, Claim 1, Line 24:
    Please replace "results in an acapsular phenotype of the bacterium thereby attenuating" --with attenuates--.

In Column 17, Claim 56, Line 34:
    Please remove "SEQ ID NO shown in"

In Column 17, Claim 57, Line 38:
    Please remove "SEQ ID NO shown in"

Signed and Sealed this

Twenty-fifth Day of November, 2008

JON W. DUDAS
*Director of the United States Patent and Trademark Office*